United States Patent
McGlothen (10) Patent No.: US 6,899,102 B1
(45) Date of Patent: *May 31, 2005

(54) STRAP FOR NASAL CANNULA AND METHOD OF HOLDING CANNULA TUBES

(76) Inventor: Roberta McGlothen, 13930 2$^{nd}$ Ave. West, Orofino, ID (US) 83544

(*) Notice: Subject to any disclaimer, the term of this patent is extended or adjusted under 35 U.S.C. 154(b) by 45 days.

This patent is subject to a terminal disclaimer.

(21) Appl. No.: 10/111,794
(22) PCT Filed: Oct. 25, 2000
(86) PCT No.: PCT/US00/41628

§ 371 (c)(1),
(2), (4) Date: Jul. 23, 2002

(87) PCT Pub. No.: WO01/34236

PCT Pub. Date: May 17, 2001

Related U.S. Application Data (63) Continuation-in-part of application No. 09/427,865, filed on Oct. 26, 1999.

(51) Int. Cl.$^7$ .............................................. A61M 15/08
(52) U.S. Cl. .......................... 128/207.18; 128/DIG. 26; 128/200.24
(58) Field of Search ............................... 128/98, 200.24, 128/204.18, 206.27, 207.11, 207.14, 707.18, 207.04–207.18, DIG. 26, 208.28, 204.11, 204.12, 206.11

(56) References Cited

U.S. PATENT DOCUMENTS

| | | | | |
|---|---|---|---|---|
| 3,726,275 A | * | 4/1973 | Jackson et al. ......... | 128/207.18 |
| 3,802,431 A | * | 4/1974 | Farr ....................... | 128/207.18 |
| 4,106,505 A | * | 8/1978 | Salter et al. ............ | 128/207.18 |
| 4,836,200 A | * | 6/1989 | Clark ..................... | 128/207.18 |
| 4,995,384 A | * | 2/1991 | Keeling .................. | 128/207.18 |
| 5,704,916 A | * | 1/1998 | Byrd .......................... | 604/179 |
| 6,536,436 B1 | * | 3/2003 | McGlothen ............. | 128/207.18 |

* cited by examiner

Primary Examiner—Glenn K. Dawson
(74) Attorney, Agent, or Firm—Pedersen & Co., PLLC; Ken J. Pedersen; Barbara S. Pedersen (57) ABSTRACT

A securement device for a nasal cannula having a nosepiece and first and second cannula tubes. An elongated strap having a first end and a second end and a first surface and a second surface. The first end encircling the first cannula tube behind and below a user's one ear, and the second end encircling the second cannula tube behind and below the user's other ear. The elongated strap first surface has a strip of hook fastener and a cooperating strip of loop fastener near the first end. The first surface has a strip of hook fastener and a cooperating strip of loop fastener near the second end. The strips of hook fastener being adjacent to their respective cooperating strips of loop fastener on the first surface without space between them. The first end encircles the first cannula tube and attaches to itself to form a loop around the first cannula tube with an interior surface, and the second end encircles the second cannula tube and attaches to itself to form a loop around the second cannula tube with an interior surface. The interior surface being covered substantially entirely with the strips of hook fastener and loop fastener.

8 Claims, 7 Drawing Sheets

STRAP FOR NASAL CANNULA AND METHOD OF HOLDING CANNULA TUBES

This application claims priority, and is a U.S.C. 371 national entry, of PCT Application PCT/U00/41628, international filing date Oct. 25, 2000, and also is a CIP of U.S. Non-Provisional patent application Ser. No. 09/427,865, U.S. filing date Oct. 26, 1999, which is the priority application for said PCT Application.

BACKGROUND OF THE INVENTION

1. Field of the Invention

This invention relates generally to nasal cannula devices for assisting breathing in humans. More specifically, this invention relates to a convenient and inexpensive strap, and methods, for securely but comfortably holding the nasal cannula to the head of the wearer, in a discreet and unobtrusive way that prevents accidental dislodgement and interruption of supplemental oxygen.

2. Related Art

Many people wear nasal cannula to assist them in breathing. Typically, pure oxygen or air enriched in oxygen is provided under slight positive pressure through plastic tubes to the nostrils of the wearer of the cannula. This way, more oxygen is provided to the lungs of the wearer.

The nasal cannula, however, must be securely held in place under the nostrils of the wearer. Typically, a nosepiece is partially inserted into the nostrils, and the cannula tubes extend from the nosepiece back over the top of the ears, around the ears and down together along the front of the chest to the oxygen supply. This conventional securement of the cannula often causes discomfort for the wearer. Typically, chafing of the oxygen tubes on the cheeks and over the ears of the wearer are experienced when prior art securement techniques are utilized. Also, the cannula often may be easily dislodged during sleeping or resting, reducing its effectiveness. Also, because the cannula is uncomfortable, some patients are more likely to purposely remove it or to leave it off when it becomes dislodged. Several devices have already been invented to address this discomfort and security problem.

For example, U.S. Pat. Nos. 2,259,817 (Hawkins), 2,292,568 (Kanter et al.), and 4,333,143 (Foster) disclose straps which encircle the head to hold a cannula in place. Also, U.S. Pat. Nos. 5,117,818 (Palfy) and 5,653,228 (Byrd '228) disclose straps which support additional, separate securing devices for holding a device next to the face. Palfy includes a strap as part of a complex system, wherein the strap extends from two car loops of a gastric feeding tube holder around the back of the head generally above the ears. Finally, U.S. Pat. No. 5,704,916 (Byrd '916) discloses a strap which extends over the top of the head and holds the cannula up off the ears with clips at the end of the strap, and U.S. Pat. No. 4,836,200 (Clark) discloses a strap that extends over a user's head and lifts oxygen tubes upwards from the top of the user's cars.

Still there is a need for a convenient and inexpensive securement means for holding the nasal cannula securely but comfortably to the head of the wearer, but with less structure than prior art devices. This invention addresses that need.

This invention is a simple, and inexpensive strap for stabilizing a nasal cannula on a wearer. Preferably, the strap has both hook and loop fasteners at each end. The strap is attached directly to both of the oxygen tubes behind the ears, and rests on the lower back of the head, no higher than the earlobe and preferably behind and below the earlobe, or the nape of the neck of the wearer. This way, the cannula may be conveniently and securely attached to the head of the wearer, while providing increased comfort relative to prior art systems. The invention accomplishes these objects in a discreet manner with lightweight apparatus that is minimally visible to the patient and to others.

SUMMARY OF THE INVENTION

The present invention comprises a convenient and inexpensive strap, and a method, for securely and comfortably holding a nasal cannula to the head of a wearer. Preferably, the strap is made of a substantially non-stretchable, cloth or fabric, most preferably Tyveck® material, about ½ in. (1.3 cm) wide and 9½ to 12 in. (24 to 30 cm) long. The strap has detachable attachment mechanisms at each end, so that it may be easily attached to conventional cannula tubes preferably without any intermediate apparatus between the strap and the cannula tubes. The strap is adjustable and/or has adjustable attachment mechanisms for shortening or lengthening the length of the strap. Preferably, the strap has a ½ in. (1.3 cm) strip of hook fastener, and a 3 in. (7.6 cm) strip of loop fastener at each end on one same side of the cloth. To use the strap, one end of it is looped and secured to itself around one of the oxygen tubes, at a position on the oxygen tube generally between the ear and the shoulder. The strap extends behind the cars of the wearer, and rests on the lower back of the head generally below the ears, at about the nape of the neck of the wearer. The second end of the strap is looped around the other oxygen tube and secured to itself, in a mirror-image position between the other ear and other shoulder of the patient. Thus, the strap attaches at both ends to the cannula tubes generally below the ears, so that the strap rests where most people have a hollow, inwardly-contoured area that is located where the head contours to the neck. When positioned in this inwardly-contoured area, the strap resists being brushed or pulled out of position and does not slip off its position on the head. Also, when a wearer rests his/her head against a pillow or other support, the strap is not significantly compressed between the user's skin and a pillow or support, because of its position in the contour of the head/neck, rather than on the protruding back of the head. Therefore, the strap is unlikely to bruise or hurt the head. Also, because of its preferred position below the protruding back of the head, in a hollow "H," rather than on a protrusion of the head or over the top of the head, the strap does not slip out of position.

When in use, the invented strap is preferably entirely below the patient's ears and is substantially behind the patient's ears. The strap preferably does not encircle any part of the patient's body, except that the strap tends to curve around the back of the neck, that is, about ⅓–½ way around the neck. The tension in the strap may be adjusted to pull the tubes in slightly towards the middle of the back of the head or neck. Thus, the strap may be positioned so that it pulls the tubes slightly off of the back of the ears, but is not positioned so that it lifts the tubes up off of the top of the ears. While preferably holding the cannula off of the back of the ears and holding the cannula from falling off the ears, the invented strap preferably still allows some movement of the cannula, relative to the user's ears, the neck, and the strap itself. This way, the cannula may be conveniently and securely attached to the head of the wearer, while giving the user both a more secure and comfortable feeling without giving the user a "strapped-in" feeling. Further, the invented method and strap provide comfortable securement without bulky and obtrusive apparatus. The invented method places the compact strap in a position that is barely visible, if at all, from the front of the user as the user rests on a bed or sits in a chair. The strap is substantially or entirely concealed behind the person, depending on the adjustment of the strap and its resulting length, without portions extending over or in front of the head. This allows the user to feel more natural in the use of the cannula and less concerned about his/her appearance while using the cannula.

DESCRIPTION OF THE PREFERRED EMBODIMENTS

Referring to the Figures, there is depicted one, but not the only, embodiment of the invented cannula holding device and methods for holding a cannula. As illustrated in the Figures, the invented strap 5 is a simple, efficient system for increasing security and comfort for oxygen cannula wearers. The invented strap need only be connected to the cannula tubes, and need not be attached to the nosepiece of the cannula. The invented strap helps insure that the cannula tubes will not fall off or become pulled off the ears. The invented strap increases comfort because it reduces/eliminates the chafing of the cannula tubes on the ears, because it prevents significant movement of the cannula tubes relative to the user's skin. The invented device and method work because it is inherently more comfortable to wear a cannula system if the cannula tubes are not shifting in position and the cannula nosepiece is not shifting/shaking in the nostrils, with every slight movement of the wearer.

FIGS. 1–4 illustrate the preferred design and use of the invented strap 5. The preferred embodiment attached directly to the cannula tubes, and includes no band or attachment around any portion of the user's body, no strap over the user's head, and no attachment to any other clothing or apparatus besides the left and right oxygen-conduit cannula tubes.

Figure 1A:
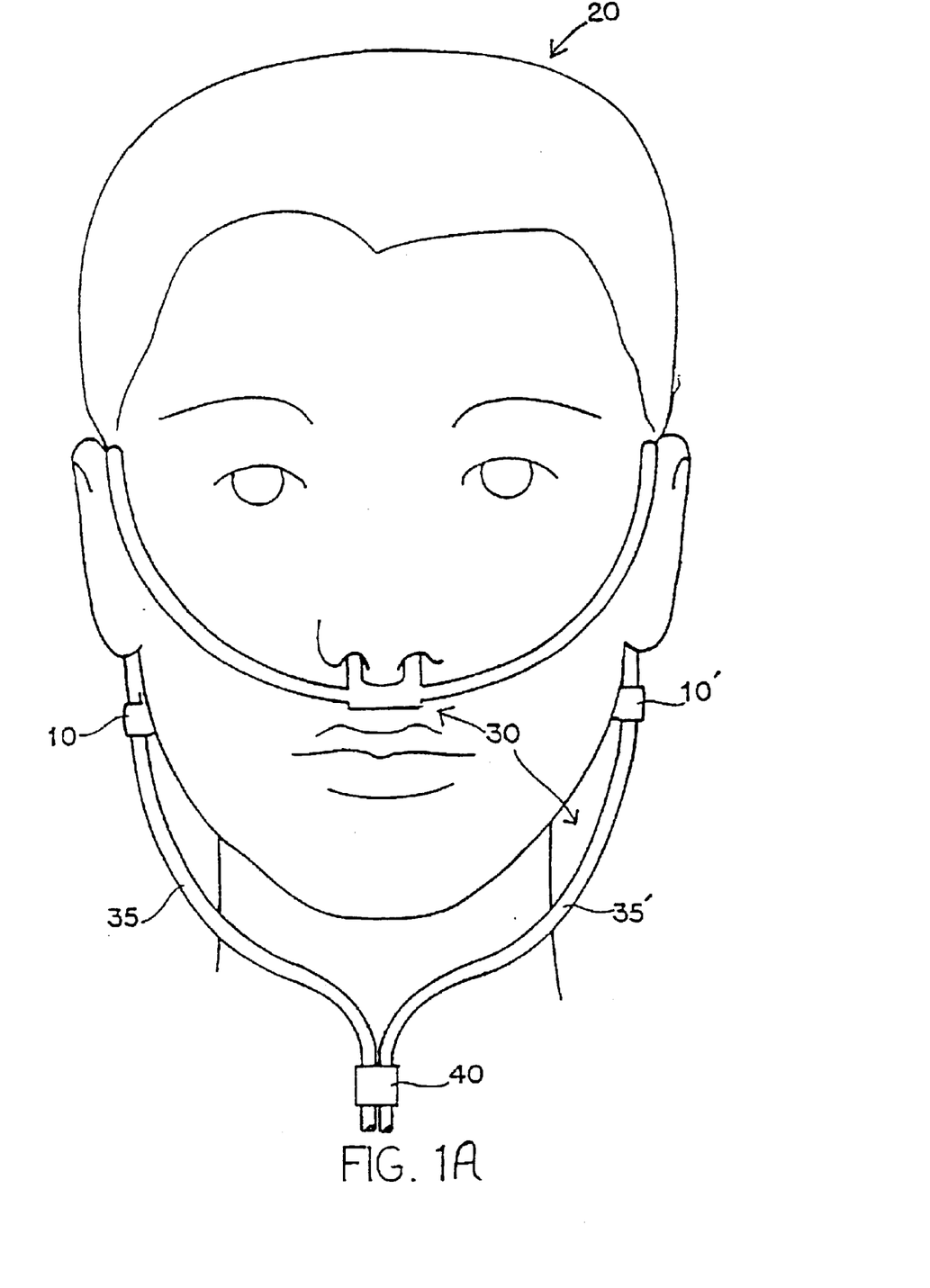
FIG. 1A is a front view of a user wearing an embodiment of the invented strap for holding cannula tubes.

On front view FIG. 1A, strap loops 10 and 10' of the invention may be seen beneath the ears on each side of and behind the wearer's 20 head. The FIG. 1A position is a less-preferred, lower and non-tensioned position. Nasal cannula 30 has hollow, plastic tubes 35 and 35' which extend from both of the wearer's nostrils, up over both cheeks beneath the eyes, up over both ears, and down over the front of both shoulders to be joined by clip 40 at the front of the chest. Then, the cannula tubes 35 and 35' extend to an oxygen source (not shown). In FIG. 1A, the strap 5 is positioned and tightened only to an extent that the ends of the loops 10, 10' show when one is looking straight at the wearer from the front, whereas the more preferred positions involve the higher and more tensioned position of FIGS. 1B and 1C.

Figure 1B:
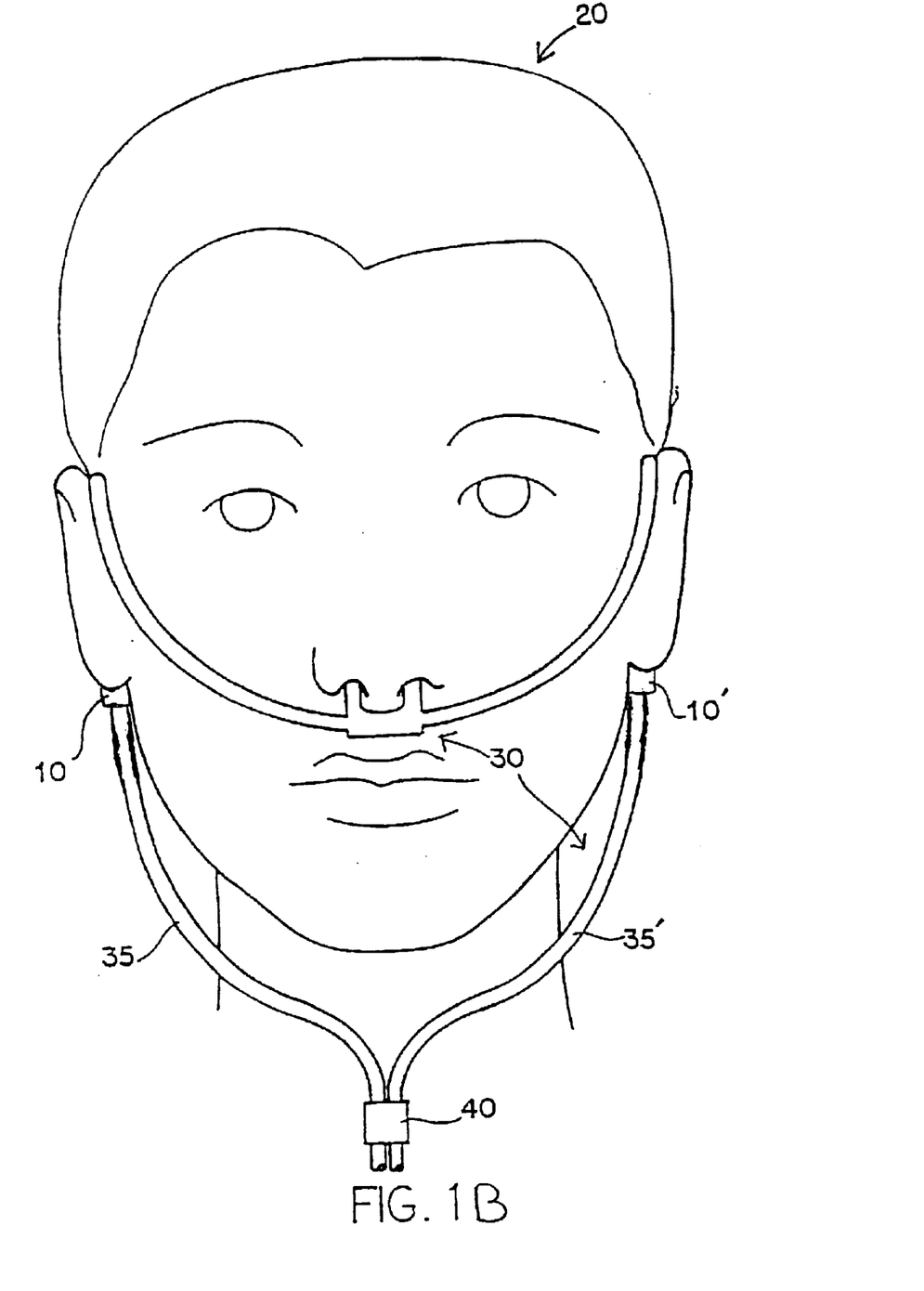
FIG. 1B is a front view of a user wearing the embodiment of FIG. 1A in a more tensioned and higher position, wherein the strap is substantially hidden from view from the front.
Figure 1C:
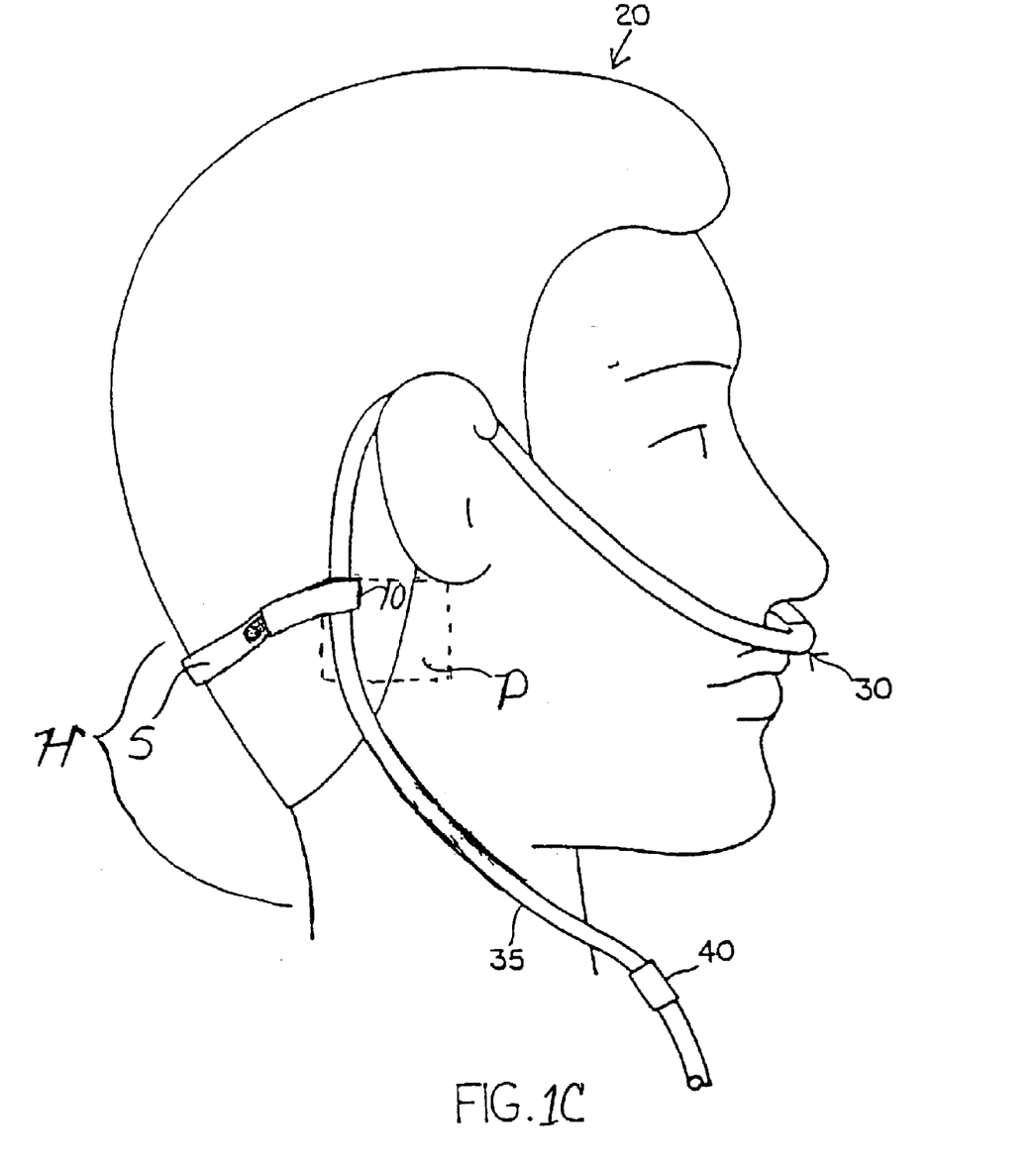
FIG. 1C is a side view of the user wearing the embodiment of FIG. 1B in the tensioned higher position.

In FIGS. 1B and 1C, the strap 5 is positioned in a higher position and slightly tensioned relative to FIG. 1A, illustrating the more preferred position and condition of strap placement. In this position, as shown in FIGS. 1B and 1C, the strap and its loops 10, 10' are nearly invisible to a front observer and the strap tends to pull the cannula tubes slightly off of the back of the ears. In the extreme, the strap is positioned at or slightly below the level of the earlobe and tensioned to an extent that places the strap substantially back from the ears wherein the strap is substantially or entirely invisible when the user is viewed from the front.

Figure 2:
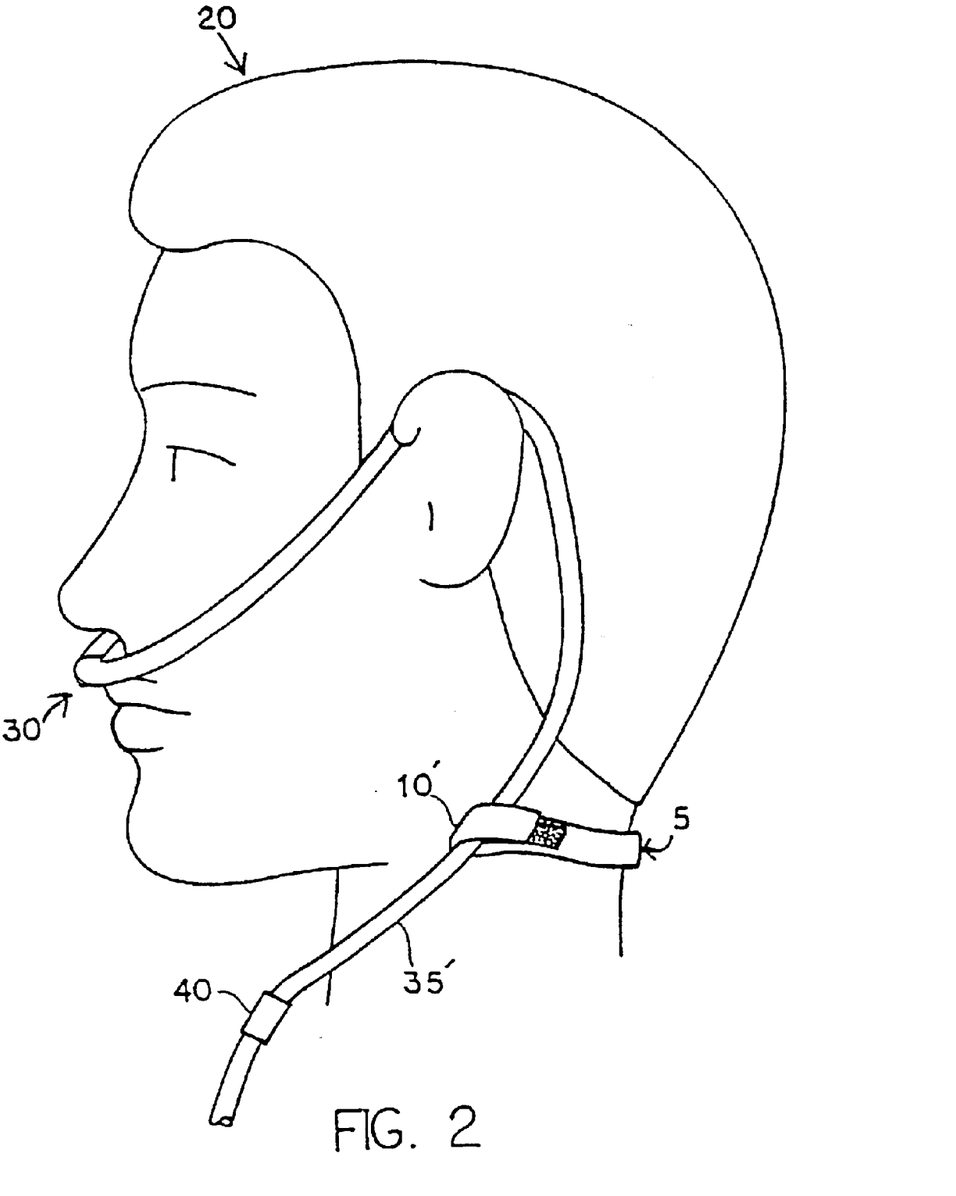
FIG. 2 is a left side view of a user wearing the strap of FIGS. 1A–C, with the strap in a lower position on the nape of the neck.
Figure 3:
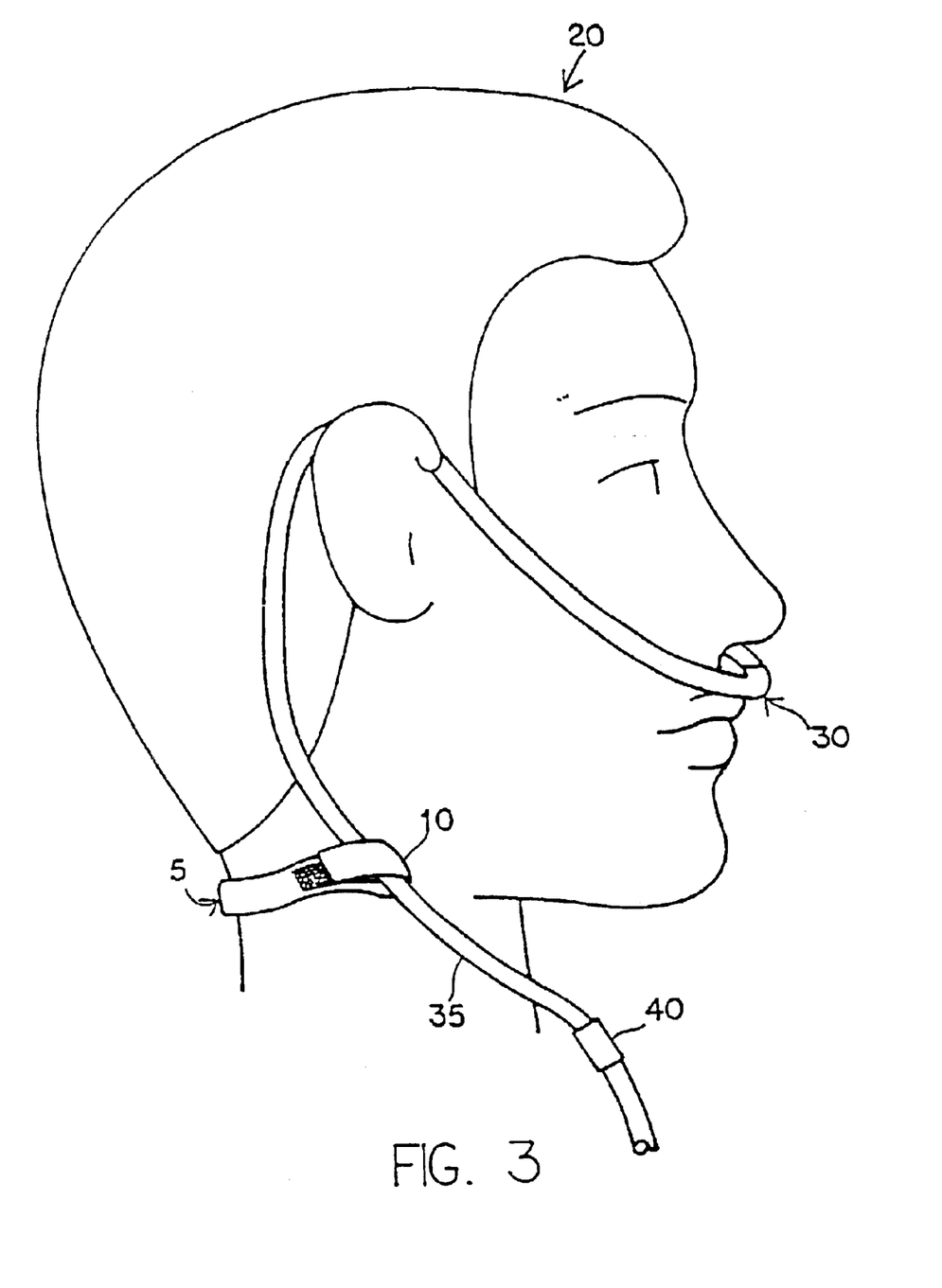
FIG. 3 is a right side view of the user wearing a strap according to the invention in a position as in FIG. 2.

In the views of FIGS. 2 and 3, the strap 5 is positioned down somewhat, relative to the placement in FIGS. 1A, 1B, and 1C, which is a position that may be comfortable for some wearers depending on the shape and size of their head and neck. In left side view FIG. 2, strap 5 and left side strap loop 10' of the invention may be seen beneath the left ear and behind the head, respectively, of the wearer 20. Cannula 30 with left tube 35' and clip 40 also appear in this Figure. In FIG. 2, strap 5 and left side strap loop 10' are worn on a lower position on the head than in FIG. 1.

In right side view FIG. 3, strap 5 and right side strap loop 10 of the invention may be seen beneath the right ear and behind the head, respectively, of the wearer 20. Cannula 30 with right tube 35 and clip 40 also appear in this Figure. In FIG. 3, strap 5 and right side strap loop 10 are worn at the same location as in FIG. 2.

Figure 4:
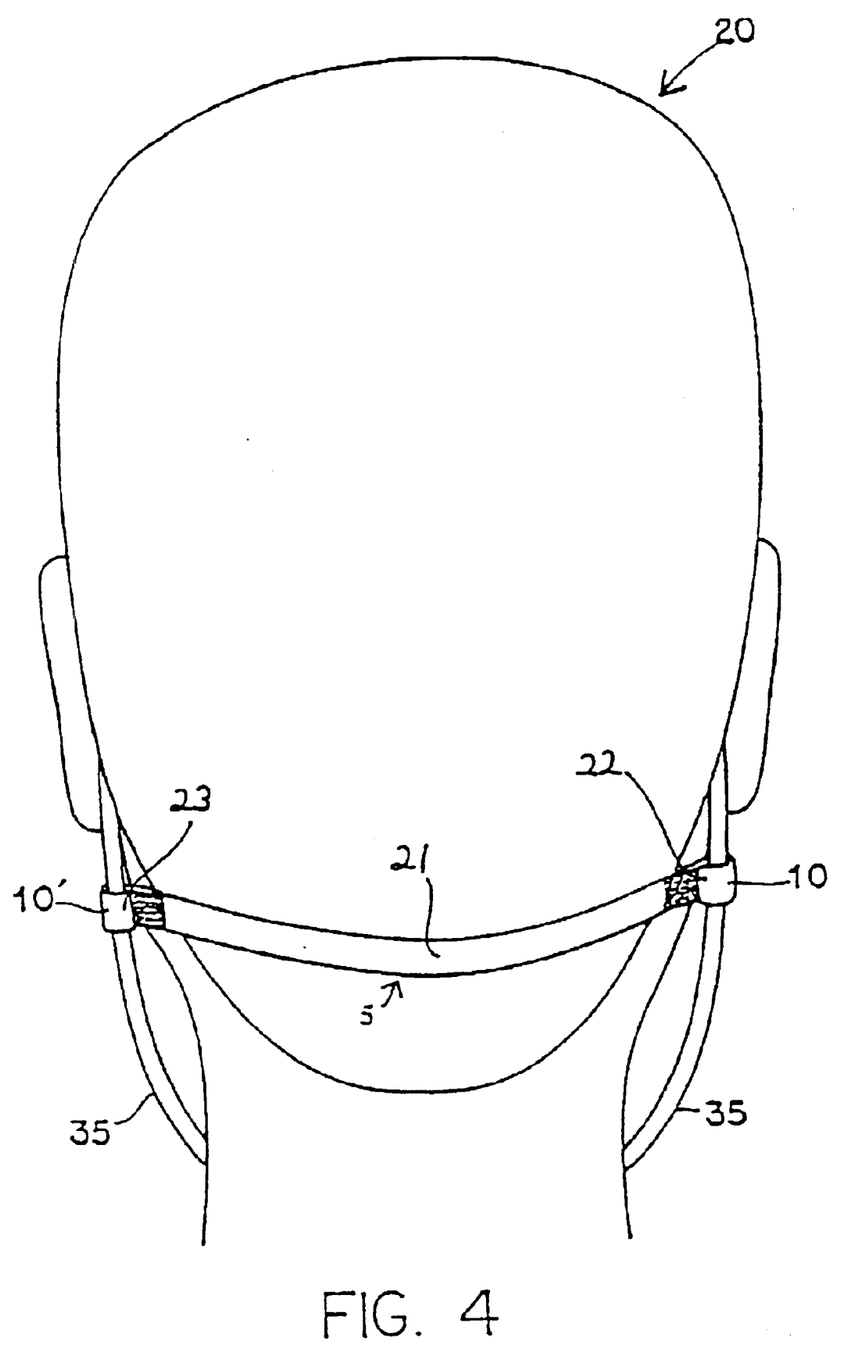
FIG. 4 is a back view of a user wearing a strap according to the invention in the position of FIG. 1A.

In back view FIG. 4, strap 5, left side loop 10' and right side loop 10 of the invention may be seen beneath the ears and behind the head of wearer 20, with the strap 5 up in the position of FIG. 1A. Cannula left tube 35' and right tube 35 also appear in this Figure.

One may see from the Figures that several positions are acceptable for strap 5, and these positions depend on personal preference and the size and shape of the wearer's head, neck and ears, and the position of the ears. The strap in all positions is generally horizontal when the wearer is standing or sitting vertically upright, which includes positions in which the loops 10, 10' are slightly above the center of the strap. Thus, by locating the strap loops, one is, in effect, also describing the position of the strap center. The strap is positioned "generally below the ears," which phrase means that the strap may be positioned so that:

the strap loops 10, 10' are within a range from a) the ear lobe, that is, at most $V_2$ in. (1.3 cm) up from the lowermost surface of the ear lobe to b) nearer the shoulders so that the strap rests midway down on the nape of the neck; or the strap is more preferably "below the ears," which phrase means that the strap is entirely below the ears, and is positioned so that:

the strap loops 10, 10' are within a range from a) just below the lowermost surface of the ear lobe to b) nearer the shoulders so that the strap rests midway down on the nape of the neck.

Also, the strap is positioned "generally behind the ears," which phrase means that:

the strap with its loops extends only as far forward as the vertical midline of the ears and rearward from there.

More preferably, the strap is positioned "behind the ears," which phrase means that:

the strap with its loops are entirely behind the ears.

Thus, there is a range of locations for the invented strap and its methods of use, depending of the wearer and need for securement. The especially-preferred strap and methods place the attachment points of the strap, for example, the preferred loops 10, 10' within an area "P" directly below and behind the earlobe that is about one inch square (2.54×2.54 cm). This area P may also be described as the recessed area directly behind and below the earlobe that is substantially between the rear of the jawbone and the neck musculature. The preferred placement of the strap is which no part of the strap above the level of the earlobes. Because the end of the human nose is typically at or slightly above the level of the ear lobes, the preferred strap placement results in the strap and loops 10, 10' being lower on the body than the end of the nose.

Figure 5:
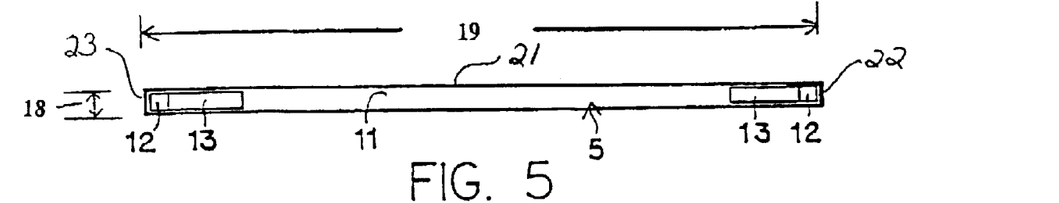
FIG. 5 is a schematic outside surface view of an embodiment of the invention.

In schematic view FIG. 5, strap 5 is depicted with width 18 (about $V_2$ inch (1.3 cm)) and length 19 (about 9–12 inches (23–30 cm)). Strap 5 is preferably a single, elongated, one-piece strap, without apertures and without loops other than the distal end loops 10, 10'. The strap is preferably made of a generally soft cloth or foam material, so that it does not necessarily require additional pads or cushions to be added to the strap for touching the patient's skin. A non-stretchable material is greatly preferred, to prevent stretching that might allow the cannula tubes to shift off the ears, dislodge the nosepiece, and defeat the purpose of the strap. Also, the width of about ½ inch (1.3 cm) is preferred because a wider strap will tend to longitudinally fold over on itself, and a narrower strap will tend to cut into the skin.

Outside surface 11 of the strap 5 has center 21 and distal ends 22, 23, each of which distal ends 22, 23 may be said to comprise a "distal area" at the outermost end of the strap and an "inner area" slightly closer to the center 21. The strap has abutting strips of both hook section 12 and loop section 13 fasteners at each of the distal ends 22, 23. Typically, hook section 12 is at the "distal area" of each distal end 22, 23 of surface 11, and is shorter (about ⅙ times) than the length of loop section 13, which is located at the more proximal "inner area" of the ends 22, 23. Typically, hook section 12 is about ½ inch (1.3 cm) long, and loop section 13 is about 3 inches (7.6 cm) long. Typically, strap 5 and hook and loop sections 12 and 13, respectively, are all approximately the same width.

The preferred configuration of hook and loop fasteners may therefore be described as being all on a single surface of the invented strap, with no hook and loop fasteners, or fasteners of any kind, on the other surfaces of the strap. The hook section is adjacent to the loop section without any significant gap in between, so that the hook and loop material is substantially continuous along up to about 3½ inches (9 cm) along each end of the strap. In this way, each loop 10, 10' around its respective cannula tube has an interior surface surrounding the cannula tube that is covered substantially entirely with hook and loop fastener. This positioning of the book and loop fasteners and the inherent frictional nature of the hook and loop fasteners allows a significant range of adjustment of the tightness of the connection between the loops 10, 10' and the cannula tubes. For example, if a non-restrictive connection is desired, the loops 10, 10' may be made to be generally loose on the cannula tubes, or, if a more restrictive connection is desired, the loops 10, 10' may be tightened around the tubes. In this latter, restrictive connection, the small diameter of the loop and the frictional surface of the hook and/or loop fastener material contribute to the restrictive nature of the connection. Thus, it is not necessary or desired to provide a glued, taped, or other integral attachment of the strap 5 to the cannula tubes.

The above-described configuration of hook and loop fasteners allows securement of the cannula without complex structure. The invented system is a single, generally horizontal strap 5 that extends from cannula tube to cannula tube. There is no need for buckle mechanisms, and no need for the strap ends 22, 23 to meet or overlap. There is no need for any of the strap structure to extend forward across the patient's cheeks, lips, nose, or forehead. In its typical use, the forward-most portion of the invented strap, also the upward-most portion of the strap, is the loop 10, 10' around the cannula tubes.

Figure 6:
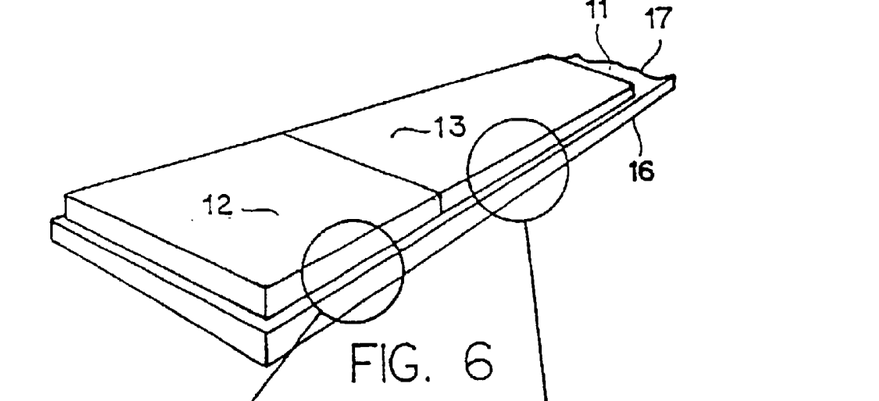
FIG. 6 is a schematic partial perspective view, including two magnified detail views, FIGS. 6A and 6B.
Figure 6A:
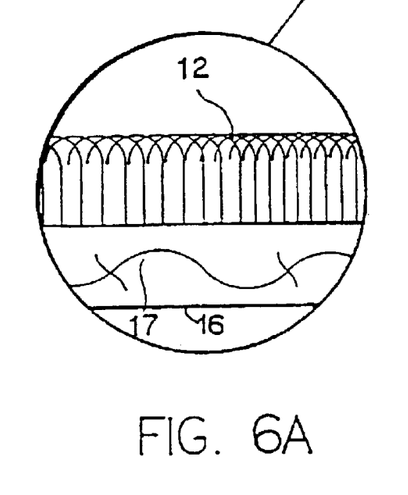
Figure 6B:
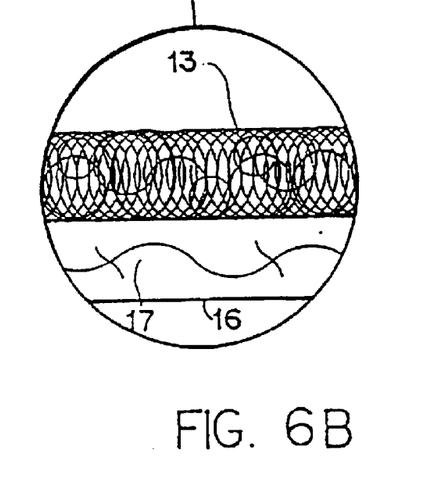

In schematic partial view FIG. 6 including FIGS. 6A and 6B, outside surface 11, and inside surface 16 of substrate 17 are seen. The long section 13 of loop material shall preferably be made long enough to accommodate a variety of patient profile dimensions. The combination of both right and left side adjustments will allow an overall adjustment range equal to the length of the longer section 13. The width 18 is sufficient to allow adequate distribution of any pressure or tension developed by attachment of the support strap 5 to the left 35' and right 35 descending tubes of the nasal cannula 30. The length 19 shall be variable depending upon the application of the strap 5 to either adults, children, or infants.

The loop (10, 10') formed by folding the short hook section 12 back on the longer loop section 13, thereby enclosing the descending tube (35, 35') and maintaining said tube's relative position in front of and to the side of the neck of the patient does not necessarily create a restrictive connection to the said descending tube. If desired, a non-restrictive connection allows moderate movement of the descending tubes through the thereby created loops and minimizes unintended pulling on the nasal cannula caused by unconscious and/or involuntary movements of the sleeping patient.

Although this invention has been described above with reference to particular means, materials and embodiments, it is to be understood that the invention is not limited to these disclosed particulars, but extends instead to all equivalents within the scope of the following claims.

I claim:

1. A method of securing nasal cannula to a wearer's head, the method comprising:

providing a nasal cannula on a wearer, the nasal cannula having a nosepiece and oxygen-conduit right and left cannula tubes extending from the nosepiece, by placing the nosepiece in the wearer's nostril's and looping the right and left cannula tubes over right and left ears of the wearer, down behind the ears, forward above the shoulders, and to the wearer's front chest;

securing the cannula tubes by attaching a securement strap to the right and left cannula tubes at a location on the tubes between a portion of the tubes looping over the ears and a portion of the tubes where the tubes extend over the shoulders so that the strap extends between the tubes behind the neck in a hollow generally between the wearer's head and neck;

and tightening the securement strap to prevent the cannula tubes from falling off of the ears.

2. The method as in claim 1, wherein the strap is tightened to pull the tubes off of the back of the wearer's ears, but does not lift the tubes up off of the top of the ears.

3. The method as in claim 1, wherein the nosepiece, tubes looping over the ears, and the securement strap are the only means for securing the cannula on the wearer.

4. The method as in claim 1, wherein the strap is attached at a location on the tubes within 1 inch below the right and left earlobes and within 1 inch behind the earlobes.

5. The method as in claim 1, wherein no part of the strap extends to a level above the wearer's earlobes.

6. The method as in claim 1, wherein the strap has a center and a strap first end and a second end, wherein the strap has a strip of hook fastener and a cooperating strip of loop fastener near the first end and the strap has a strip of hook fastener and a cooperating strip of loop fastener near the second end.

7. A method of securing nasal cannula to a wearer's head, the method comprising:

providing a nasal cannula on a wearer, the nasal cannula having a nosepiece and oxygen-conduit right and left cannula tubes extending from the nosepiece, by placing the nosepiece in the wearer's nostril's and looping the right and left cannula tubes over right and left ears of the wearer, down behind the ears, forward above the shoulders, and to the wearer's chest;

securing the cannula tubes only by the method comprising attaching a securement strap to the right and left cannula tubes at a location on the tubes below the wearer's ears so that the securement strap extends between the tubes behind the neck in a hollow generally between the wearer's head and neck;

and tightening the securement strap to prevent the cannula tubes from falling off of the ears;

so that, when the wearer rests his head on a pillow, the strap is not significantly compressed between the wearer's head and the pillow.

8. The method of claim 7, wherein the strap is positioned so that no part of the strap is above the earlobes.

* * * * *